(12) United States Patent
Bzdusek et al.

(10) Patent No.: US 10,232,192 B2
(45) Date of Patent: Mar. 19, 2019

(54) EFFICIENT TREATMENT PLAN TRADE-OFF ANALYSIS

(71) Applicant: KONINKLIJKE PHILIPS N.V., Eindhoven (NL)

(72) Inventors: Karl Antonin Bzdusek, Madison, WI (US); Sankara Hari Gopalakrishnan, Madison, WI (US); Prashant Kumar, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 339 days.

(21) Appl. No.: 15/039,048

(22) PCT Filed: Nov. 24, 2014

(86) PCT No.: PCT/IB2014/066293
§ 371 (c)(1),
(2) Date: May 25, 2016

(87) PCT Pub. No.: WO2015/083035
PCT Pub. Date: Jun. 11, 2015

(65) Prior Publication Data
US 2017/0173365 A1 Jun. 22, 2017

Related U.S. Application Data

(60) Provisional application No. 61/911,507, filed on Dec. 4, 2013.

(51) Int. Cl.
*A61N 5/10* (2006.01)
*G06F 19/00* (2018.01)
(Continued)

(52) U.S. Cl.
CPC ............. *A61N 5/103* (2013.01); *G06F 19/00* (2013.01); *G06F 19/321* (2013.01);
(Continued)

(58) Field of Classification Search
CPC ........................ A61N 2005/1041; A61N 5/103
See application file for complete search history.

(56) References Cited

U.S. PATENT DOCUMENTS 7,708,682 B2   5/2010   Pekar et al.
8,401,148 B2   3/2013   Lu et al.
(Continued)

FOREIGN PATENT DOCUMENTS

CN   1953782 A    4/2007
CN   101120871 A  2/2008

OTHER PUBLICATIONS

Oeilfke, U. et al., "Inverse Planning for Photon and Proton Beams", Medical Dosimetry, 2001, vol. 26, No. 2, pp. 113-124.
(Continued)

*Primary Examiner* — Christine H Matthews

(57) ABSTRACT

A planning image memory stores a volume diagnostic image. A user inputs data defining clinical objectives including organs-at-risk with a user interface device. An auto-planning module generates a candidate treatment plan. A trade-off module having a processor evaluates the treatment plan against the clinical objectives. When one or more objectives is not met, the trade-off module performs a trade-off analysis to determine an effect on other clinical objectives and generates at least one trade-off treatment plan which more closely meets the not met objectives. The candidate and at least one trade-off plan are displayed on a display device and/or analyzed by the processor and a final treatment plan is selected from the at least one trade-off or candidate treatment plan.

10 Claims, 2 Drawing Sheets

(51) Int. Cl.
*G16H 50/30* (2018.01)
*G06N 99/00* (2019.01)

(52) U.S. Cl.
CPC ....... *G06F 19/3481* (2013.01); *G06N 99/005* (2013.01); *G16H 50/30* (2018.01); *A61N 2005/1041* (2013.01)

(56) References Cited

U.S. PATENT DOCUMENTS

| | | |
|---|---|---|
| 9,865,048 B2 | 1/2018 | Wakai |
| 2011/0153547 A1 | 6/2011 | McNutt et al. |
| 2012/0203053 A1 | 8/2012 | Kilby et al. |
| 2013/0197878 A1 | 8/2013 | Fiege et al. |
| 2015/0087879 A1* | 3/2015 | Nelms ................ A61N 5/103 600/1 |

OTHER PUBLICATIONS

Yang, Y. et al., "Clinical knowledge-based inverse treatment planning: IMRT inverse planning", Physics in Medicine and Biology, Institute of Physics, 2004, vol. 49, No. 22, pp. 5105-5117.
Lee, E.K., "Optimization with Multiple Objectives", NCI-NSF workshop on Operations Research in Radiation Therapy, 2002, Washington, D.C., http://www2.isye.gatech.edu/nci-nsf.orart.2002/pdf-files/talk4.lee.pdf.
Bokrantz, R., "Multicriteria optimization for volumetric-modulated arc therapy by decomposition into a fluence-based relaxation adn a segment weight-based restriction", Optimization and Systems Theory, Stockholm, 2012.

* cited by examiner

EFFICIENT TREATMENT PLAN TRADE-OFF ANALYSIS

CROSS-REFERENCE TO PRIOR APPLICATIONS

This application is the U.S. National Phase application under 35 U.S.C. § 371 of International Application Serial No. PCT/IB2014/066293, filed on Nov. 24, 2014, which claims the benefit of U.S. Application Ser. No. 61/911,507, filed on Dec. 4, 2013. These applications are hereby incorporated by reference herein.

The present application relates generally to radiation therapy. It finds particular application in conjunction with radiation therapy planning and will be described with particular reference thereto. However, it is to be understood that it also finds application in other usage scenarios and is not necessarily limited to the aforementioned application.

In radiation therapy planning, creating a patient specific treatment plan can be a time consuming and tedious task. Many of the steps are redundant and vary little from patient to patient or plan to plan. Many of these steps can be automated using macro languages or scripts, but certain aspects are difficult without tools for writing logical expressions, loops, and other common programming functionality.

In the past decade, technological advancements have provided a big leap in the field of intensity modulated radiation therapy (IMRT), intensity modulated proton therapy (IMPT) and the like, to improve dose delivery. One area that is difficult to automate in current treatment planning is intensity-modulated radiation therapy (IMRT) or volumetric-modulated arc therapy (VMAT) optimization. Recently the research interest has shifted towards methods of automating various tasks involved in plan generation, starting from beam placement to dose optimization, to assist and reduce the workload burden on the clinical user. Optimization is an iterative process where a user attempts to specify planning goals in the form of dose or biological objectives to create an ideal dose to target structures, typically a uniform high dose, and minimize the dose to critical structures.

Plan evaluation is classified into three phases: 1. Physical evaluation, 2. Technical evaluation and 3. Clinical evaluation. The physical and technical aspects of a plan are generally examined by a technician after the completion of the plan. The clinical aspects of a plan are investigated by a radiation oncologist. Currently an IMRT plan is evaluated based on five categories that cover the physical, technical and clinical aspects of a plan: 1. Geometric analysis, 2. Dose distribution analysis, 3. Dose Volume Histogram (DVH) analysis, 4. Parametric analysis and 5. Deliverability analysis.

The geometric analysis is performed to evaluate the optimality of beams placement. Beam placement is a very important step. The quality of optimization is mainly influenced by the number of beams and their angles. Rules have been formulated for optimal beam placement in IMRT in view of increasing the optimality and deliverability of an IMRT plan.

The dose distribution analysis qualitatively verifies the optimality of dose distribution in axial, coronal and saggital planes. This analysis can be further split up into 2D analysis and 3D analysis. 2D dose distribution analysis implies the evaluation of dose distribution slice-by-slice. This type of analysis is used to evaluate the conformality of the prescribed dose with respect to the target volume in each slice. This type of analysis can also reveal the distribution of cold or hot spots in and around the target volume. Cold or hot spots are areas within the target and organs at risk that receive less or greater than the intended dose of radiation. The 3D distribution analysis is useful in determining how conformal a dose distribution is to the overall target volume with respect to a set of beam orientations.

Dose Volume Histograms (DVH) are a powerful tool for evaluating the optimality of a plan. A DVH represents a 3-dimensional dose distribution in a graphical 2-dimensional format. A DVH for target volume graphically represents the quality of the dose distribution in terms of coverage, conformity and homogeneity. The DVH curves for Organs-at-risk (OARs) represent the efficiency at which the OARs are spared in terms of mean and maximum dose.

The parametric analysis is performed to quantitatively verify the optimality of dose. The parameters used in this analysis are: (a) minimum, mean and maximum dose for target volume and OARs and (b) coverage, conformity and homogeneity indices for target volume. Apart from physical metrics for plan evaluation, a plurality of biological metrics are used in plan evaluation. These biological metrics include Equivalent Uniform Dose (EUD), Tumor Control Probability (TCP) and Normal Tissue Complication Probability (NTCP) and the like.

Deliverability analysis is performed in order to evaluate how robust the plan is in terms of dose delivery. This analysis involves the verification of parameters such as number of segments, minimum or average monitor units (MU) per segment, Minimum Segment Area (MSA), total delivery time and the like. MU is a measure of machine output of a linear accelerator in radiation therapy. The deliverability analysis reveals whether or not a plan is realistically deliverable.

Various stages of plan generation have been automated with different techniques. These techniques reduce the burden on the clinical user, i.e. a radiation technician, by automating the plan generation process, such as dose objective manipulation and IMRT/VMAT optimization. Given the complexity involved with radiation therapy treatment plan generation, it is imperative that the user wants a certain amount of manual control and review but at the same time it stops these techniques from being fully automatic. A current auto-planning solution offers one time configuration of user defined template which can be later applied to a new patient for automatically generating a treatment plan.

Specifically, it is difficult to determine the best plan to meet the goals since the definition of best is subjective and variable for the same user from patient to patient. After plan generation, the user weighs various tradeoffs between target goals and organs at risk goals and decides what is acceptable for each patient. Understanding the tradeoffs has been the focus of several technologies. However, one issue with the approaches is that the user has too much more flexibility than needed which makes the workflow too general and less focused for physicians. Another issue is that it is exclusive to fluence based plans only.

In accordance with one embodiment, a treatment planning system comprising: a planning image memory which stores a volume diagnostic image; a memory for storing user defined clinical objectives configured for a user to input data defining clinical objectives including organs-at-risk; an auto-planning module configured to generate a candidate treatment plan; and a trade-off module having a processor configured to: evaluate the treatment plan against the clinical objectives; when one or more objectives not met, perform a trade-off analysis to determine an effect on other clinical objectives; and generate at least one trade-off plan which more closely meets the not met objectives.

In accordance with one preferred method of the present application, a method for generating trade-off plans for radiation therapy treatment planning, comprising: generating a candidate treatment plan; evaluating the treatment plan against the clinical objectives; when one or more objectives not met, perform a trade-off analysis to determine an effect on other clinical objectives; and generating at least one trade-off plan which more closely meets the not met objectives.

In accordance with another embodiment, a treatment planning system comprising: a planning image memory which stores a volume diagnostic image; a memory for storing user defined clinical objectives configured for a user to input data defining organs-at-risk; an auto-planning module configured to generate a treatment plan; and a trade-off module having a processor configured to: evaluate the treatment plan against clinical goals; when goals not met, select organs at risk for trade-off analysis; create a copy of the treatment plan corresponding for each selected organ-at-risk; optimize the corresponding treatment plan copy according to the clinical goals for the selected organ-at-risk; evaluate the at least one trade-off plan against the clinical goals for the selected organs at risk; and select a final plan from the at least one trade-off plan and optimized plan.

One advantage is streamlined tradeoff analysis for the physician.

Another advantage is that less candidate plans are generated for increased efficiency.

A further advantage is that IMRT/VMAT planning complexity is reduced.

Another advantage is that a deliverable plan trade-off space is created that focuses on the problem areas where clinical objectives are not met by the initial plan.

Still further advantages of the present invention will be appreciated to those of ordinary skill in the art upon reading and understand the following detailed description.

Figure 1:
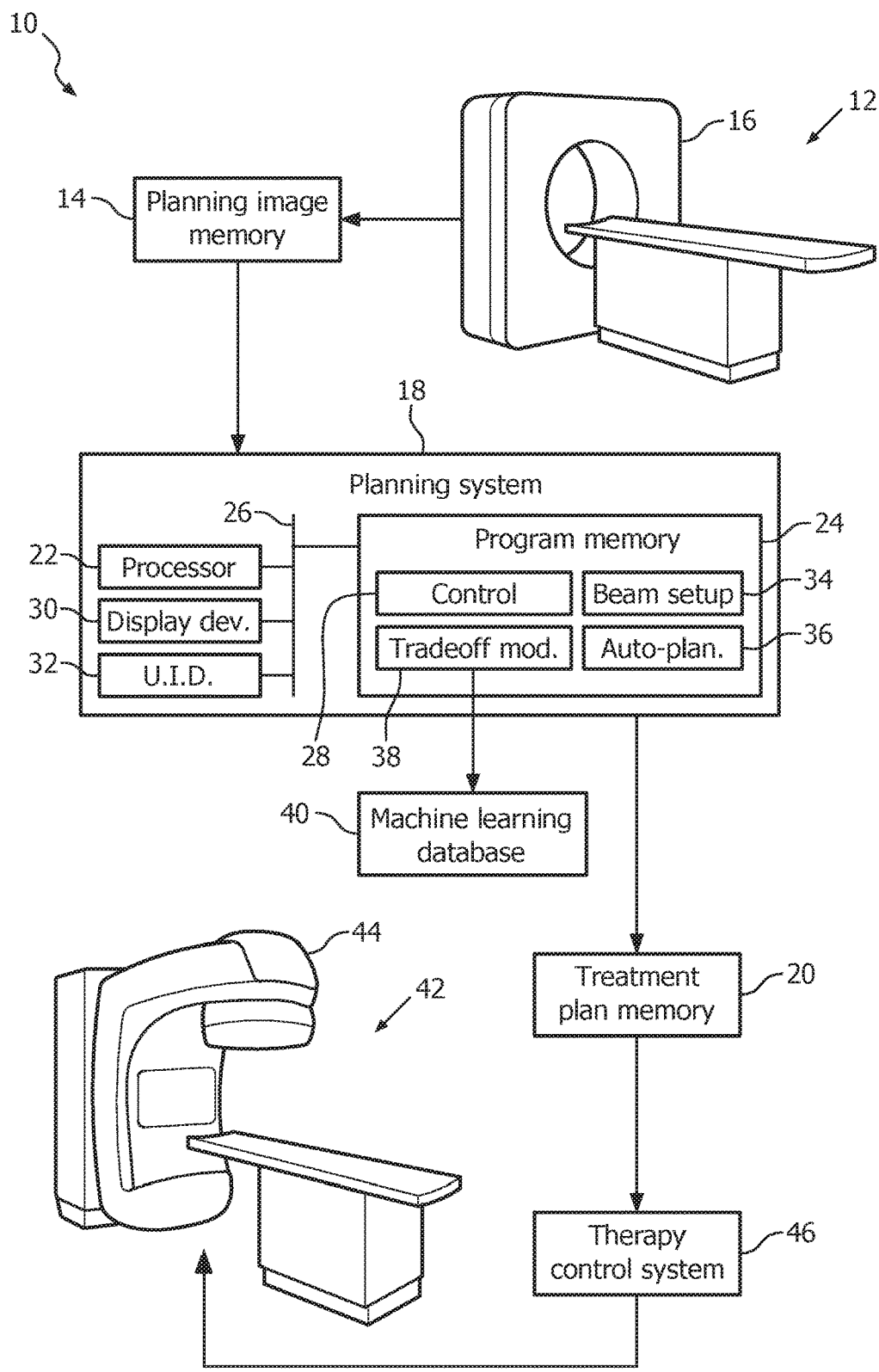
FIG. 1 depicts an IMRT planning system implementing an improved method for automating plan generation.

With reference to FIG. 1, a therapy system 10, such as an intensity-modulated radiation therapy (IMRT) system or a volumetric-modulated arc therapy (VMAT) system, includes an imaging system 12 to generate one or more planning images of a region of interest of a patient. The image volume, i.e. the planning images, is volumentric (i.e., three-dimensional) and typically stored in a planning image memory 14 of the therapy system 10. The region of interest includes one or more target structures and, typically, one or more critical structures or organs at risk (OARs). Each of the target structures is a lesion or other tissue region, such as a tumor, to be irradiated. Each of the critical structures is an organ or other tissue region which is at risk of damage from the radiation intended for the target structures, such as radiation traveling to the target structures, which has passed through the target structures, or which passes closely adjacent the target structures.

The imaging system 12 generates the planning images using one or more imaging modalities, such as computed tomography (CT), positron emission tomography (PET), magnetic resonance (MR), single photon emission computed tomography (SPECT), cone-beam computed tomography (CBCT), and the like. Hence, the imaging system 12 includes one or more scanners 16 corresponding to the imaging modalities, as well as a backend system reconstructing raw image data from the scanners into the planning images. As illustrated, the imaging system 12 generates the planning images using for example CT and includes a CT scanner 16.

A planning system 18 of the therapy system 10 generates an optimal treatment plan for the patient on the planning images, which are typically received from the planning image memory 14. The optimal treatment plan suitably includes a plurality of treatment fractions, each identifying planning target volumes (PTVs) for the target structures, margins around the target structures, dose profiles for the target structures, dose limits for the critical structures, and therapy beam directions and intensities, and is typically stored in a treatment plan memory 20 of the therapy system 10. The planning system 18 includes at least one processor 22 and at least one program memory 24. The program memory 24 includes processor executable instructions that, when executed by the processor 22, generate the optimal treatment plan. The processor 22 executes the processor executable instructions to generate the optimal treatment plan. The planning system 18 further includes at least one system bus 26 interconnecting the processor 22, the program memory 24, and any other components of the planning system 18.

A control module 28 of the processor executable instructions controls overall operation of the planning system 18, including generation of the optimal treatment plan. The control module 28 suitably displays a graphical user interface (GUI) to a user of the planning system 18 using a display device 30 of the planning system 18. Further, the control module 28 suitably allows the user to interact with the GUI using a user input device 32 of the planning system 18. For example, the user can interact with the GUI to specify parameters, controlling the generation of the optimal treatment plan. In particular, the user specifies regions of interest and organs-at-risk within the image volume located on the planning image memory 14 via the user input device 32 and other unique parameters. In one embodiment, a memory for storing user defined clinical objectives is used. The display device 30 also displays a visual presentation of trade-off values, met and unmet objectives, and specific areas of trade-off.

A therapy beam setup module 34 of the processor configures one or more therapy beams used for therapy delivery. This can be performed automatically and/or manually. As to automatic therapy beam setup, an appropriate routine is employed to automatically configure parameters configuring the therapy beam. It is also contemplated that therapy beam setup can be performed using a combination of automatic and manual therapy beam setup. Beam placement is achieved using beam angle optimization or selection methodologies along with the beam configurations followed in standard clinical practice e.g. for head and neck a standard equally spaced 7-9 beam co-planar configurations are enough. Additional provision to accept the number of beams input from the user is also possible, in which case the system only optimizes on the beam angles. Iterative adjustment of beam placements is also a possibility if the auto-plan results are not as desired. The automatically configured parameters can then be displayed to the user using the display device 30 and the user can modify the parameters, as appropriate, using the user input device 32.

Once the parameters are finalized, an auto-planning module 36 generates a candidate treatment plan. The auto-planning module 36 includes receiving input parameters for generation of the treatment parameter. The input parameters include the boundaries of the structures (i.e., the target structures and, typically, the critical structures) within the planning images, as well as therapy beam configuration parameters, which are determined using the therapy beam setup module 34. In one embodiment, automatically generating optimal treatment plans uses an algorithm such as the one described in U.S. Provisional Application Ser. No. 61/719,528 to Bzdusek, et al. It automatically drives the IMRT optimizer by formulating dose objectives and manipulating them iteratively. The dose objective parameters define the clinical goals and priorities.

Often the candidate treatment plan does not meet every goal and objective. A trade-off module 38 generates alternate trade-off plans using the clinical goals and the optimized treatment plan from the auto-planning module 36. The trade-off module 38 receives the candidate treatment plan form the auto-planning module 36. The trade-off module 38 receives clinical objectives defined by the user through the user input 32. The trade-off module 38 evaluates the candidate treatment plan against the input clinical objectives and determines if the objectives are satisfied. If the objectives are satisfied, the user selects the optimized treatment plan without the trade-off module 38 generating alternate trade-off plans.

If the trade-off module 38 determines the treatment plan does not meet all the clinical objectives, then a trade-off analysis is performed. The user reviews the trade-off determinations made by the trade-off module 38. In one embodiment, the trade-off module 38 controls the auto-planning module 36 to generate an alternate treatment plan with the unmet objectives constrained to be met or met more fully. In another embodiment, the trade-off module displays the determinations where goals are met or not met to the user on the display. The user uses the user input to explore alternate treatment plans further via a trade-off analysis. In another embodiment, the organs-at-risk are automatically selected by the trade-off module 38.

The user has the option to input priority rankings for specific objectives. In one embodiment, the priority rankings are categorized, i.e. low, medium, and high. In another embodiment, the priority rankings are relative numeric values, i.e. 1-10. The user can select the objectives and the priorities through the user input 32 and the auto-planning module 36 attempts to satisfy the higher priority goals first at the expense of lower priority goals. In one embodiment, the trade-off module 38 raises the ranking of the unmet objectives to see how the candidate treatment plan changes. In one embodiment, the priorities and selected organs-at-risk are selected to a predetermined plan template.

In one embodiment, the trade-off module 38 performs trade-off analysis by generating at least one alternate plan using the already generated treatment plan as a starting point. Using the generated plan saves time and effort in recreating plans from the beginning. In one embodiment, the trade-off module 38 copies original generated plan for each organ-at-risk or other goal that is not met or selected. The trade-off module 38 drives the optimization algorithm to meet, or more closely meet, the unmet goals by changing the optimization parameters for the specific organ-at-risk. Once the goals are met for the specific organ-at-risk, the trade-off module 38 attempts to meet the rest of the goals for the remaining organs-at-risk. In one embodiment, the trade-off module 38 attempts to meet the remaining goals while optimizing to meet the goals for the specific organ-at-risk. The trade-off module 38 creates a plurality of alternate trade-off plans corresponding to each unmet goal for each selected organ-at-risk. The generated trade-off plans show the effect of meeting one of the goals on the rest of the goals for the target and organ-at-risk structures. In one embodiment, trade-off plans are generated for a combination of unmet organ-at-risk goals. In another embodiment, the plans utilize anchor plans that consider all organs-at-risk and target structures in the optimization and only optimizes up to a minimum acceptable goal. For example, the generated candidate treatment plan exceeds the minimum acceptable dose for a lower priority objective by a large margin while a higher priority objective was not met. The trade-off module 38 uses the candidate treatment plan to meet the high priority objective first, then optimizes the lower priority objective to a minimum acceptable dose.

After the trade-off plans are generated, the trade-off module 38 performs further trade-off analysis for comparing plans to each other. The user uses plan comparison features such as dose volume histogram (DVH) overlap or side by side trial dose to evaluate the trade-offs in the trade-off plans. In one embodiment, dose estimates for plans are created by interpolating between two dose grids using a mixing parameter to control the level of interpolation.

In one embodiment, the user selects from one of the alternate trade-off plans or the candidate plans to be delivered to the patient. In another embodiment, the final plan is selected automatically by the trade-off module 38. After the plan is selected, the trade-off module 38 optionally updates a machine learning database 40 with the selected plan for use in future IMRT planning. For example, the selected plan stored in the database can be used as an already generated trade-off plan in the future when the objectives for an organ-at-risk are not met.

A delivery system 42 executes the selected treatment plan to deliver therapy, such as ablation therapy, external beam radiation therapy and/or brachytherapy, to the patient. The therapy typically includes radiation, such as one or more of x-rays, protons, high-intensity focused ultrasound (HIFU), and the like. The delivery system 42 includes a delivery apparatus 44, such as a linear particle accelerator, and a control system 44, which controls the delivery apparatus 46 in accordance with the optimal treatment plan. The optimal treatment plan is typically received from the treatment plan memory 20, but other sources are contemplated.

Figure 2:
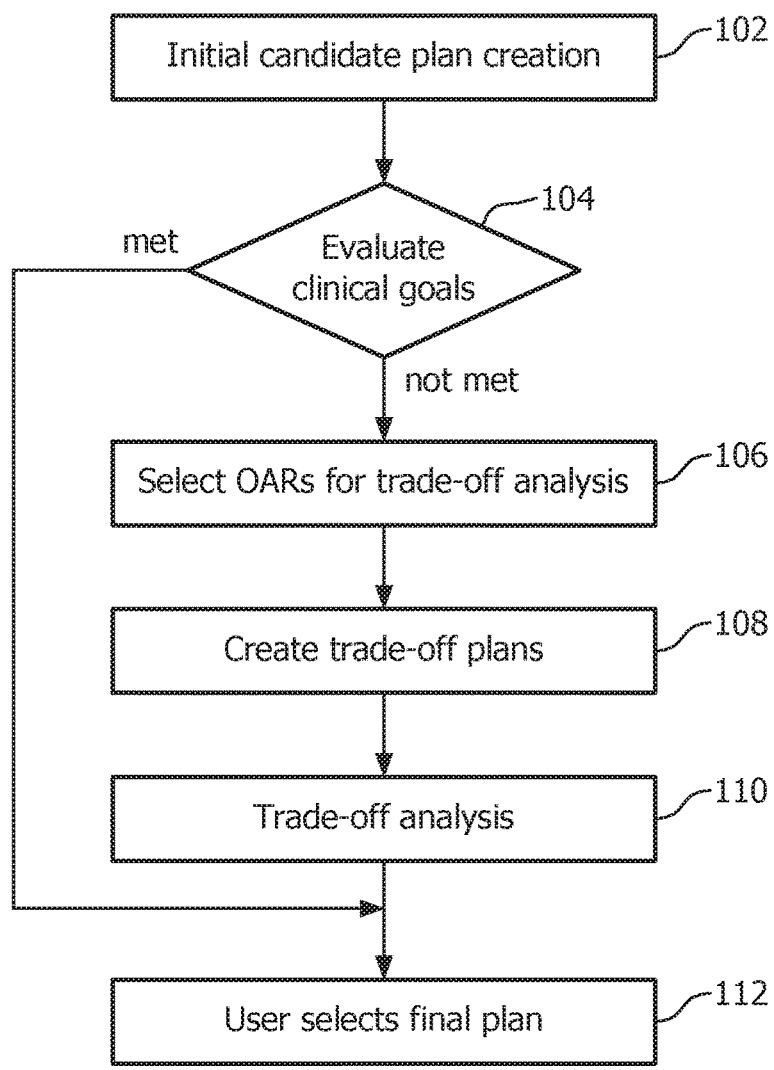
FIG. 2 depicts a method for generating trade-off plans.

FIG. 2 depicts a method for generating trade-off plans. At a step 102, an initial candidate optimized treatment plan is generated and accessed by the trade-off module 38. At a step 104, the candidate optimized treatment plan is evaluated against clinical objectives. The clinical objectives can be received by the trade-off module 38 from the user through the user input 32 or from a plan template that dictates the desired organ-at-risk goals. The optimized plan is evaluated to make a determination if all clinical goals are satisfied by the plans.

When at least one clinical goal is not met by the candidate optimized treatment plan, trade-off analysis is performed. At a step 106, organs-at-risk are selected for trade-off analysis. The organs-at-risk are selected when the goals, typically maximum dose goals, for the organ-at-risk are not met. The user can select the organ-at-risk for analysis, or it can be selected through a template or predetermined criteria.

At a step 108, at least one trade-off plan is created by the trade-off module 38. The trade-off plans are generated by first using the optimized treatment plan as a basis for efficiency. In one embodiment, a new plan could be fully reoptimized from the start. The optimized treatment plan is copied by the trade-off module, and then optimized to satisfy the clinical goals for the selected organ-at-risk, e.g. reduce radiation dose to an organ-at-risk which receives higher than optimal dose in the candidate treatment plan. It is appreciated that multiple plans can be created during this step, such as by reducing the dose for different organs-at-risk. In one embodiment, priority rankings are used when multiple organs-at-risk are selected and the trade-off plan is created based on the priority.

At a step 110, further trade-off analysis is performed. In one embodiment, the trade-off module 38 performs the trade-off analysis. Alternatively, the user performs the trade-off analysis. The generated trade-off plans are compared to each other and the optimized treatment plan. Amongst the multiple options, at a step 112, the user selects a final plan for delivery to the patient. Further during this step, a machine-learning database can be updated according to the treatment plan selected. The machine learning database 40 can be consulted to recommend one or more of the treatment plans.

It is appreciated that a user may exercise increased control of the automatic plan generation by confirming automatically determined selections after some or all of the steps. As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field programmable gate array (FPGA), and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a liquid crystal display (LCD), a light emitting diode (LED) display, a plasma display, a projection display, a touch screen display, and the like.

Although the system and method of the present disclosure have been described with reference to exemplary embodiments thereof, the present disclosure is not limited to such exemplary embodiments. Rather, the system and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. A treatment planning system comprising:
a planning image memory which stores a volume diagnostic image of a subject;
a memory for storing user defined clinical objectives configured for a user to input data defining the clinical objectives including a target dose and organs-at-risk doses;
a processor configured to:
generate a candidate treatment plan based on the clinical objectives;
evaluate the candidate treatment plan against the clinical objectives;
for each of the clinical objectives that are not met, generate a trade-off treatment plan which more closely meets each of the not met clinical objectives;
determine an effect which each of the trade-off treatment plans has on met and other not met clinical objectives; and
at least one of (i) control a display to display at least a part of the volume diagnostic image indicating doses the candidate and each trade-off treatment plan delivers to a target and to each of the organs-at-risk so that a user can select among the candidate and trade-off plans to be used to treat the subject and (ii) re-evaluate the candidate and the trade-off plans against the clinical objectives.

2. A treatment planning system comprising:
a planning image memory which stores a volume diagnostic image;
a memory for storing user defined clinical objectives configured for a user to input data defining the clinical objectives including a target and organs-at-risk and;
at least one processor configured to:
generate a candidate treatment plan based on the clinical objectives;
evaluate the candidate treatment plan against the clinical objectives;
when one or more of the objectives are not met, perform a trade-off analysis to determine an effect on met and other not met clinical objectives;
receive a priority ranking for each objective; and
generate a plurality of trade-off plans which meet higher priority objectives and meet lower priority objectives to different degrees.

3. The system according to claim 2, further including:
a display device configured to display the trade-off plans to the user showing trade-off areas and values.

4. The system according to claim 2, wherein the at least one processor is further configured to:
evaluate the trade-off plans using dose volume histogram overlap analysis.

5. The system according to claim 2, wherein the at least one processor is further configured to:
update a machine learning database based on the plurality of trade-off plans.

6. A method for generating trade-off plans for radiation therapy treatment planning, comprising:
in one or more memories, storing a volume diagnostic image;
with an input device, inputting user-defined clinical objectives including a target and organs-at-risk and priorities for the clinical objectives;
storing the user-defined clinical objectives and the priorities in the one or more memories;
with one or more processors, generating a candidate treatment plan based on the clinical objectives including the target, the organs-at-risk, and the priorities;
with the one or more processors, evaluating the candidate treatment plan against the clinical objectives and the priorities;
with the one or more processors, when one or more of the objectives are not met, performing a trade-off analysis to determine an effect on met and not met clinical objectives;
with the one or more processors, generating a plurality of trade-off plans which meet higher priorities and lower priority objectives to different degrees; and controlling a display device to display the plurality of trade-off plans showing trade-off areas and values in conjunction with at least a portion of the diagnostic image.

7. The method according to claim 6, wherein generating the candidate plan includes:
   automatically formulating the clinical objectives including dose profiles and the priorities corresponding to the target and the organs-at-risk;
   optimizing a plurality of treatment plan parameters based on the higher and lower priority objectives to generate the candidate treatment plans; and
   generating the trade-off plans includes:
      reformulating the clinical objectives including at least one of modifying parameters of the clinical objectives and/or adding one or more additional objectives to the clinical objectives; and
      repeating the optimizing based on the reformulated clinical objectives to reformulate the trade-off plans.

8. The method according to claim 6, further including:
   reevaluating the trade-off plans against the clinical objectives for the organs-at-risk.

9. The method according to claim 8, further including:
   selecting a plan from the trade-off plans and the candidate treatment plan.

10. A non-transitory computer readable medium carrying software for controlling the one or more processors to perform the method of claim 6.

* * * * *